United States Patent [19]
Hayafuji

[11] Patent Number: 5,776,061
[45] Date of Patent: Jul. 7, 1998

[54] NONCONTACT TONOMETER

[75] Inventor: Mineki Hayafuji, Tokyo, Japan

[73] Assignee: Kabushiki Kaisha Topcon, Tokyo, Japan

[21] Appl. No.: 558,195

[22] Filed: Nov. 15, 1995

[30] Foreign Application Priority Data

Nov. 16, 1994 [JP] Japan .................... 6-281943

[51] Int. Cl.$^6$ ........................ A61B 3/16
[52] U.S. Cl. ........................ 600/401; 600/405
[58] Field of Search ................ 128/648, 645, 128/652; 600/398, 401, 405

[56] References Cited

U.S. PATENT DOCUMENTS

| | | | |
|---|---|---|---|
| 5,042,484 | 8/1991 | Hideshima | 128/648 |
| 5,048,526 | 9/1991 | Tomoda | 128/648 |
| 5,465,123 | 11/1995 | Iijima | 128/648 |
| 5,487,386 | 1/1996 | Wakabayashi et al. | 128/660.01 |

*Primary Examiner*—Lee S. Cohen
*Assistant Examiner*—Eric F. Winakur
*Attorney, Agent, or Firm*—Finnegan, Henderson, Farabow, Garrett & Dunner, L.L.P.

[57] ABSTRACT

A noncontact type of tonometer is provided which includes air injection device (70) for jetting a fluid from a nozzle (18) onto a cornea (C) of a subject's eye (E), an alignment light projecting optical system (30) for projecting a beam of light onto the cornea (C), and a corneal deformation detecting optical system (60) for detecting the deformation of the cornea (C). The number of times up to which the air injection device (70) has jetted the fluid is counted by a counter (82), and the count is displayed on a monitor (M).

8 Claims, 5 Drawing Sheets

5,776,061

1

NONCONTACT TONOMETER

BACKGROUND OF THE INVENTION

1. Field of the Invention

This invention relates to a noncontact type of tonometer in which a cornea of a subject's eye is deformed by pulsed air jetted from a nozzle and, based on a quantity of deformation of the eye, intraocular pressure of the eye is measured.

2. Description of the Prior Art

Conventionally, in a noncontact type of tonometer, a beam of light is first projected onto a cornea of an eye and then light reflected by the cornea is received by a light sensor, while pulsed air is jetted from a nozzle to the cornea so as to deform the surface of the cornea. Based on a quantity of light received by the light sensor and based on air pressure jetted from the nozzle, intraocular pressure of the eye is measured.

In this tonometer, a piston within a cylinder connected to the nozzle is slid up to jet pulsed air from the nozzle. Accordingly, when the piston is slid down, the outside air is inhaled into the cylinder through the nozzle. Together with the outside air, tears scattered when the pulsed air is jetted that include impurities, are also taken in. As a result, the tears adhere to the nozzle or pass through the nozzle and adhere to a glass, or the like, disposed behind the nozzle. Repeated adhesion of the tears thereto results in a decrease of the quantity of light projected onto the cornea through the nozzle and the glass and, therefore, the decrease of the quantity of light reflected by the cornea and received by the light sensor through the nozzle and the glass. This causes a gross measurement error or an unmeasurable state.

One of countermeasure against this disadvantage is having, an operator wash stained parts of the nozzle or glass based on his/her experimental judgment. However, since it is difficult to ascertain how much of the nozzle or glass is stained with dirt such as tears, the measurement is frequently made under a state where the nozzle or glass is stained. Therefore, disadvantageously, the measurement must be repeated.

Another problem resides in that a used air-injector is not opportunely replaced by new one because the replacement is made not according to frequency of use but according to duration of use.

SUMMARY OF THE INVENTION

It is an object of the present invention to provide a noncontact tonometer which is capable of objectively ascertaining an opportunity for washing a nozzle or a glass. It is another object of the present invention to provide a noncontact tonometer which is capable of opportunely replacing an old air-injector by new one.

The present invention is characterized by a noncontact tonometer comprising a means for jetting a fluid from a nozzle onto a cornea of a subject's eye, a means for projecting a beam of light onto the cornea, a means for detecting the deformation of the cornea, and a means for counting the number of times which the fluid jetting means has jetted the fluid.

Further, the present invention is characterized by a noncontact tonometer comprising a means for jetting a fluid from a nozzle onto a cornea of a subject's eye, a means for projecting a beam of light onto the cornea, a means for detecting the deformation of the cornea, a means for counting the number of times which the fluid jetting means has jetted the fluid, and a means for, in accordance with the number of times counted by the counting means, regulating a quantity of light projected by the light projecting means.

Further, the present invention is characterized by a noncontact tonometer comprising a means for jetting a fluid from a nozzle onto a cornea of a subject's eye, a means for projecting a beam of light onto the cornea, a means for detecting the deformation of the cornea, a means for counting the number of times which the fluid jetting means has jetted the fluid, and a means for, in accordance with the number of times counted by the calculating means, regulating the detection sensitivity of the corneal deformation detecting means.

DETAILED DESCRIPTION OF THE PREFERRED EMBODIMENTS

Embodiments of a noncontact tonometer according to the present invention will be described hereinafter with reference to the attached drawings.

Figure 1:
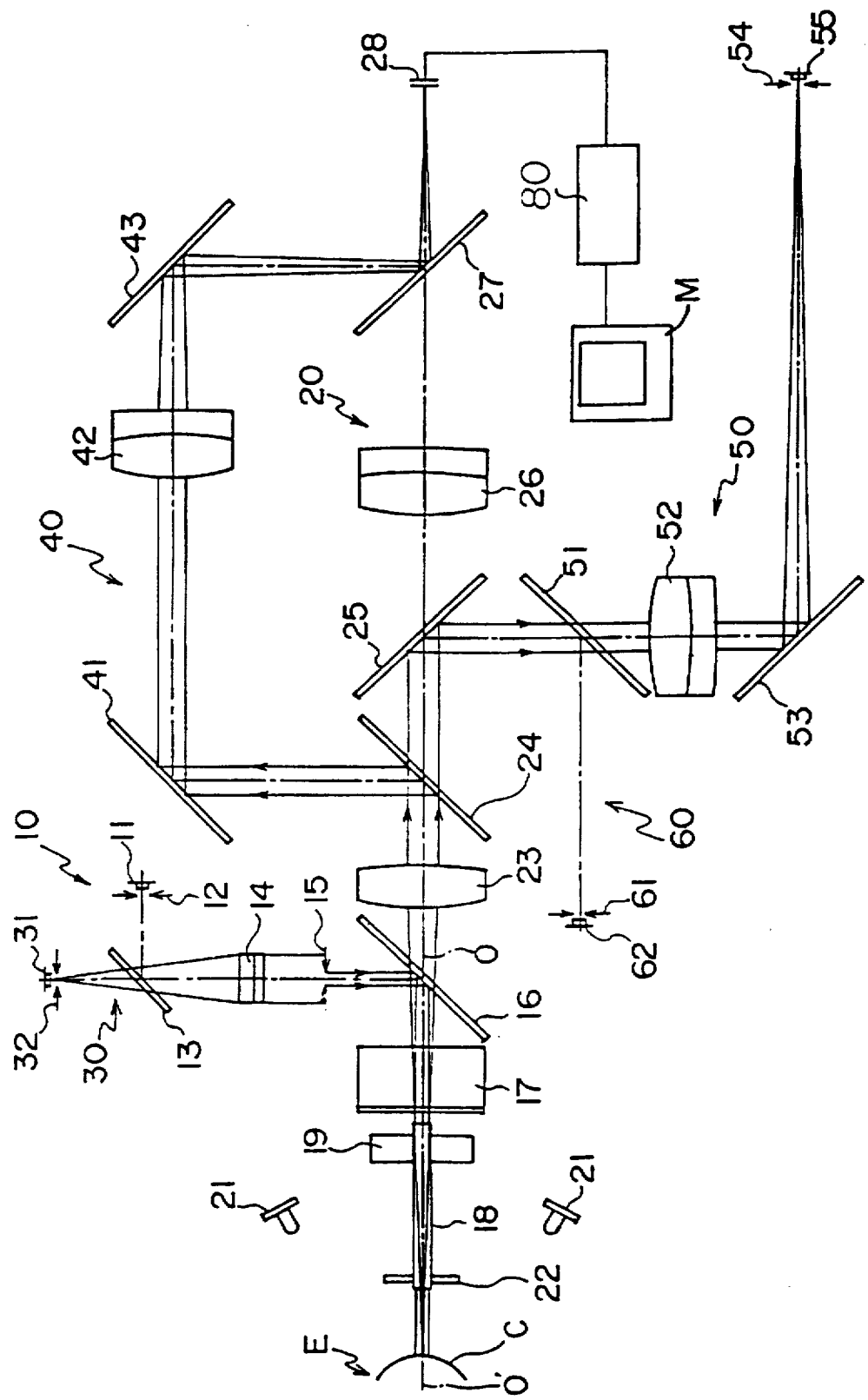
FIG. 1 is a schematic view of optical systems of the noncontact tonometer according to the present invention, mainly showing beams of light for alignment passing through the optical systems.
Figure 2:
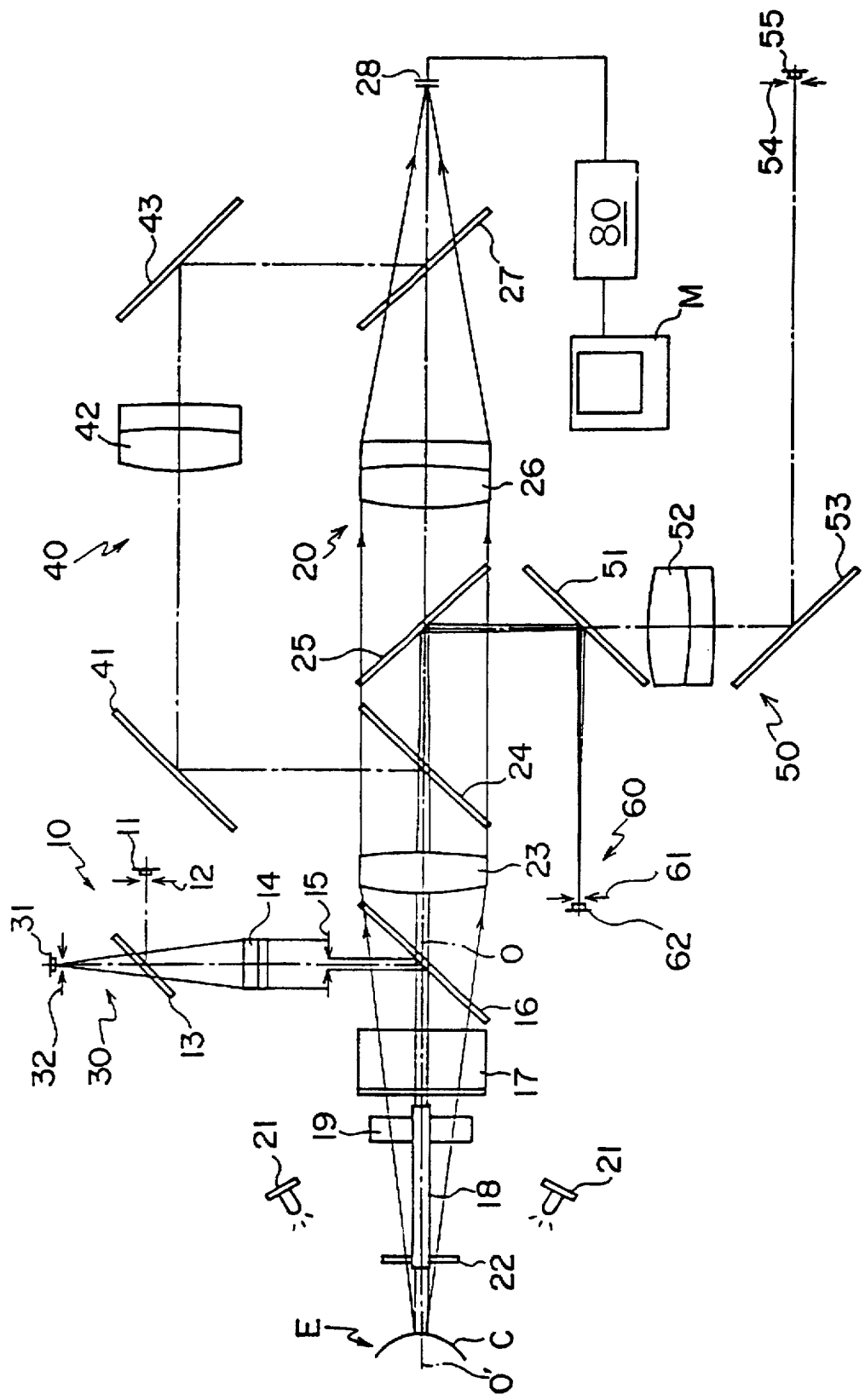
FIG. 2 is a schematic view of optical systems of the noncontact tonometer according to the present invention, mainly showing beams of light for detecting the deformation of the cornea and beams of light for observing an anterior part of the eye.

Referring to FIGS. 1 and 2, reference numeral 10 designates a target projecting optical system for projecting a target (fixation point), on which a subject's eye E is fixed, onto the eye E, and reference numeral 20 designates an anterior segment observing optical system for observing an image of an anterior segment of the subject's eye E. Reference numeral 30 designates an alignment light projecting optical system (alignment light projecting means) for projecting a beam of light for alignment onto the subject's eye E, and reference numeral 40 designates an alignment state observing optical system for observing a state of alignment between a visual axis O' of the subject's eye E and an optical axis O of the anterior segment observing optical system 20. Reference numeral 50 designates an alignment detecting optical system for detecting the alignment of an instrument body with respect to the subject's eye and, at the same time, detecting a working distance therebetween, and reference numeral 60 designates a corneal deformation detecting optical system (corneal deformation detecting means) for optically detecting the deformation of a cornea C of the subject's eye.

The target projecting optical system 10 includes an LED 11 which emits visible light, an aperture spot 12, a wavelength dividing filter 13 which reflects visible light and transmits near infrared light, a collimator lens 14, a diaphragm 15, a half mirror 16, a chamber window 17, and an injection nozzle 18.

Figure 4:
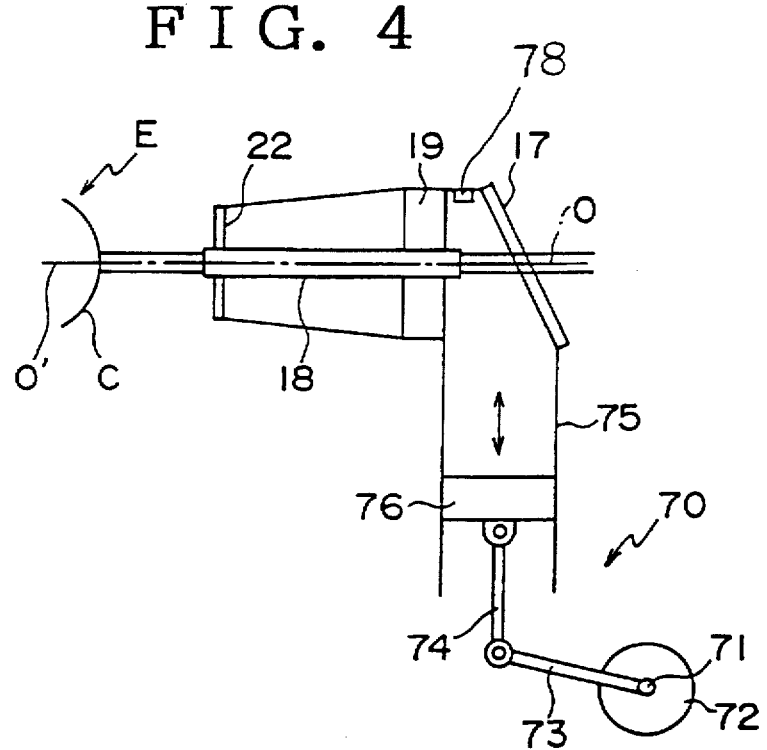
FIG. 4 is a schematic view of an air injector.

The injection nozzle 18 is supported by a transparent supporting plate 19. The chamber window 17 and the transparent supporting plate 19 are fixed to a cylinder 75 of an air injection device (fluid jetting means) 70, as shown in FIG. 4, and are each a component part of the cylinder 75.

Visible light, which is used as a target (fixation point), emitted by the LED 11 passes through the aperture spot 12 disposed at a focal point of the collimator lens 14 and then is reflected by the wavelength dividing filter 13. The reflected light is converted to parallel rays of light by the collimator lens 14. The parallel rays of light are converted to a diaphragm image by the diaphragm 15 and, without changing a state of the diaphragm image, are reflected by the half mirror 16. The diaphragm image passes through the chamber window 17 and injection nozzle 18. Thereafter, the diaphragm image reaches an eyeground (eye fundus) through the cornea C of the subject's eye E and appears thereon. The subject's eye is directed to and fixed on the diaphragm image (target).

The anterior segment observing optical system 20 includes LEDs 21 which emit infrared light by illuminating the eye E from right and left, a cover glass 22 fastened to the tip of the injection nozzle 18, the transparent supporting plate 19, the chamber window 17, the half mirror 16, an objective lens 23, a half mirror 24, a dichroic mirror 25, an image formation lens 26, a half mirror 27, and a CCD camera 28.

The objective lens 23 serves to transmit beams of light emitted by the LEDs 21 and an LED 31 and reflected by the cornea C and serves to reflect visible light emitted by the LED 11 and reflected by the cornea C so as not to guide the visible light to the optical members disposed after the objective lens 23.

The infrared light (diffusing light) emitted by the LED 21 and reflected by the eye E passes through the cover glass 22, the transparent supporting plate 19, the chamber window 17, and the half mirror 16 and then is converted to parallel rays of light by the objective lens 23. The parallel rays of light pass through the half mirror 24 and the dichroic mirror 25, and then are condensed by the image formation lens 26. The condensed light passes through the half mirror 27 and is imaged on the CCD camera 28.

An image of the anterior segment of the eye E formed on the CCD camera 28 is displayed on a monitor (display means) M via a control unit 80.

The alignment light projecting optical system 30 includes an LED 31 which emits near infrared light and is used as a light source for detection, an aperture stop 32, the wavelength dividing filter 13, the collimator lens 14, the diaphragm 15, the half mirror 16, the chamber window 17, and the injection nozzle 18.

The optical members ranging from the LED 31 to the injection nozzle 18 of the alignment light projecting optical system 30 also serve as those of a detection light projecting optical system for projecting detection light onto the cornea C to optically detect the deformation of the cornea C caused by the jet of pulsed air from the injection nozzle 18.

The near infrared light from the LED 31 passes through the aperture stop 32 and the wavelength dividing filter 13 and then is converted to parallel rays of light by the collimator lens 14. The parallel rays of light are converted to a diaphragm image by the diaphragm 15. The diaphragm image is reflected by the half mirror 16 and then passes through the chamber window 17 and the injection nozzle 18. The diaphragm image which has passed through the injection nozzle 18 reaches the cornea C of the eye E and is reflected by the cornea C.

The alignment state observing optical system 40 includes the injection nozzle 18, the chamber window 17, the half mirror 16, the objective lens 23, the half mirror 24, a total reflection mirror 41, an image formation lens 42, a total reflection mirror 43, the half mirror 27, and the CCD camera 28.

Figure 3:
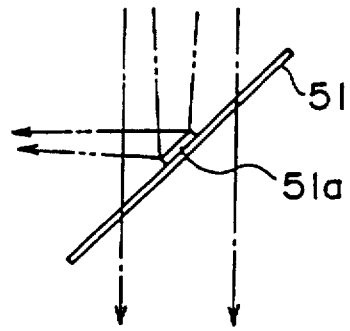
FIG. 3 is an enlarged view of an oblique transparent plate shown in FIG. 1.

The alignment detecting optical system 50 includes the optical members ranging from the injection nozzle 18 to the half mirror 24 of the alignment state observing optical system 40, the half mirror 25, an oblique transparent plate 51 having a total reflection mirror 51a in the middle of the plate 51 (see FIG. 3), an image formation lens 52, a total reflection mirror 53, a diaphragm 54, and a light sensor 55 as a light receiving means. The alignment detecting optical system 50 is used for alignment between the visual axis and the optical axis and for adjustment of a working distance.

Alignment light (diffusion light) reflected by the cornea C passes through the injection nozzle 18, the chamber window 17, and the half mirror 16 and then is converted to parallel rays of light by the objective lens 23. The parallel rays of light are guided to the half mirror 24.

Part of the light guided to the half mirror 24 is reflected by the half mirror 24. This light (alignment reflection light) reflected by the half mirror 24 is used as light for observing and detecting the alignment. The other part of the light guided to the half mirror 24 passes through the half mirror 24.

The alignment reflection light reflected by the half mirror 24 is reflected by the total reflection mirror 41 and is guided to the image formation lens 42 by which the alignment reflection light is condensed. The condensed light is reflected by the total reflection mirror 43 and the half mirror 27, and then is imaged on the CCD camera 28. This image is displayed on a monitor M simultaneously with the image of the anterior segment of the eye E described above. On the other hand, the alignment reflection light which has passed through the half mirror 24 is reflected by the half mirror 25 and then passes through the oblique transparent plate 51, as indicated by the alternate long and short dash line in FIG. 3. The alignment reflection light is then guided to the image formation lens 52 and is condensed thereby. The condensed light is reflected by the total reflection mirror 53, is imaged on the diaphragm 54 and then strikes the light sensor 55.

The magnification of the image formation lens 52 is higher than that of the image formation lens 42. Therefore, light that is easy to see and low in magnification is imaged on the CCD camera 28 when alignment is observed, whereas light high in sensitivity and magnification is guided to the light sensor (detection sensor) 55 through the diaphragm 54 when alignment is detected. The light sensor 55 outputs a detection signal to the control unit 80.

It is possible to remove the diaphragm 54 and dispose a CCD camera or the like, in place of the light sensor 55, at the position where the diaphragm 54 was disposed and, based on a position and size of an image of received light, to detect the alignment. It is also possible to alternately turn on and off the LED 31 at regular intervals and, based on a position and size of an image of received light obtained on the CCD camera 28 used for observation, detect the alignment. If this method is adopted, the alignment detecting optical system 50 can be removed.

The corneal deformation detecting optical system 60 includes the injection nozzle 18, the chamber window 17, the half mirror 16, the objective lens 23, the half mirror 24, 25, the total reflection mirror 51a, a diaphragm 61, and a light sensor 62 serving as a light receiving means.

The air injection device (fluid jetting means) 70 comprises a cylinder 75, a piston 76 sliding up and down within the cylinder 75, a rotary solenoid 72 for reciprocating the piston 76, and the like. A shaft 71 of the rotary solenoid 72 is connected to the piston 76 via a crank arm 73 and a connection arm 74, so that the piston 76 can be reciprocated within the cylinder 75 in accordance with the drive of the rotary solenoid 72. A pressure sensor 78 for detecting pressure within the cylinder 75 is disposed on the top (in FIG. 4) of the cylinder 75.

Figure 5:
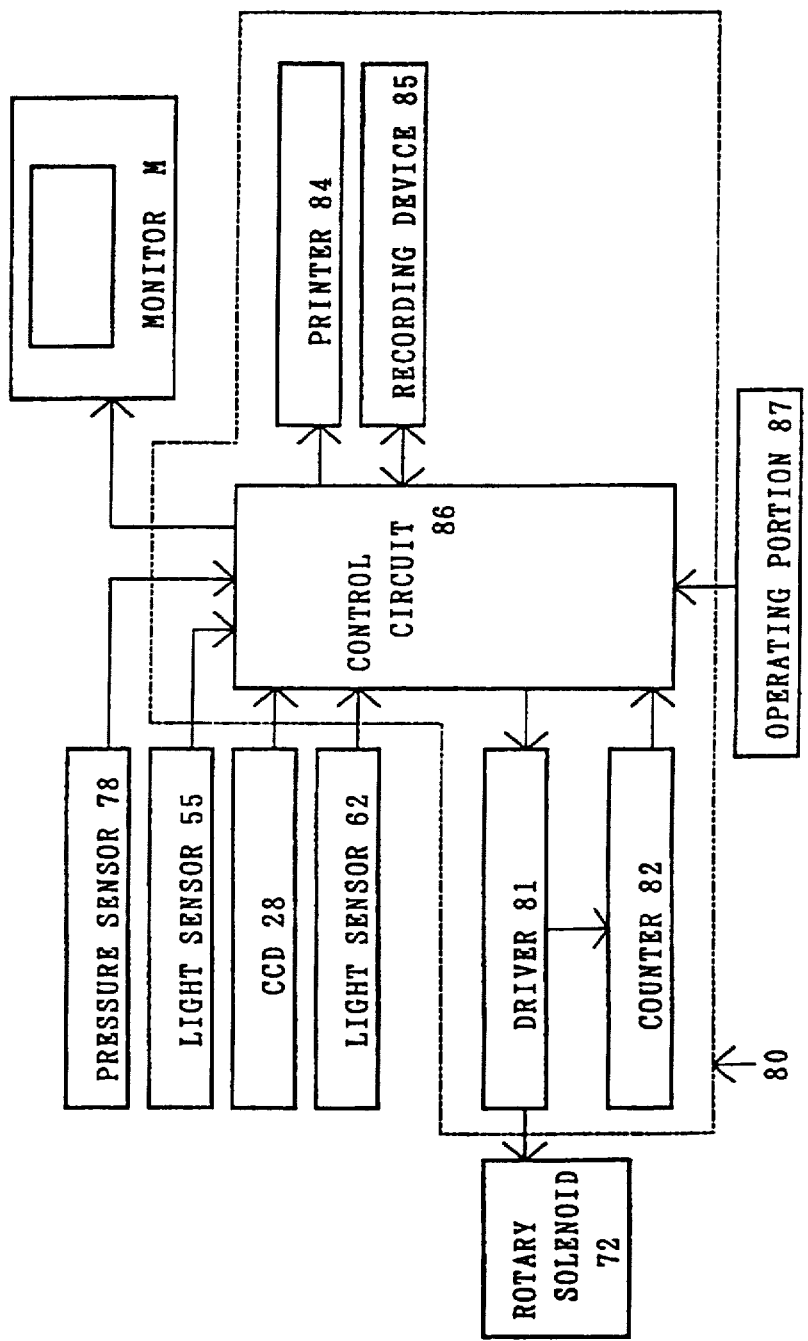
FIG. 5 is a block diagram of a control system of the noncontact tonometer shown in FIG. 1.

FIG. 5 is a block diagram showing a construction of the control unit 80. Reference numeral 81 designates a driver which drives the rotary solenoid 72, and reference numeral 82 designates a counter (counting means) for ascertaining how many times pulsed air has been jetted from the injection nozzle 18 by counting up whenever the rotary solenoid 72 is driven. In the counter 82, counting is continued unless the counter 82 is reset. Reference numeral 84 designates a printer which prints out measured eye-pressure and the like, reference numeral 85 designates a recording device which records measured data and the like, and reference numeral 86 designates a control circuit comprising a CPU for controlling the driver 81, the printer 84, the recording device 85, etc. through the operation of an operating portion 87.

The control circuit 86 causes the monitor M to display the number of counts of the counter 82 and, based on a detection signal output by the light sensor 55, detects the completion of alignment and, in addition, measures the eye pressure from both the quantity of light received by the light sensor 62 and the cylinder pressure detected by the pressure sensor 78.

Actions in the above embodiment will now be described.

First of all, the LEDs 21, 11, 31 are turned on to display an image of the anterior segment of the eye E on the monitor M, and alignment is adjusted while watching the anterior segment image. After that, based on detection signals output by the light sensor 55, the control circuit 86 detects alignment in X-Y directions (in up, down, right, and left directions) and alignment in Z direction (in a direction relative to a working distance).

After detecting the alignment, an operator operates a measurement starting switch (not shown) of the operating portion 87. Responding thereto, the control circuit 86 actuates the driver 81 on condition that the alignment has been detected.

The operation of the driver 81 brings about the drive of the rotary solenoid 72 and, as a result, the piston 76 is slid up (in FIG. 4) within the cylinder 75. By this movement of the piston 76, pulsed air is jetted (discharged) from the nozzle 18 onto the cornea C, so that the apex of the cornea C is deformed (flattened). When jetted, the anterior segment which has been deformed is displayed on the monitor M through the anterior segment observing optical system 20.

The reflection light (parallel rays of light), reflected by the deformed cornea C, for detecting the deformation of the cornea C passes through the nozzle 18, the chamber window 17, and the half mirror 16 and then is condensed by the objective lens 23. The condensed light passes through the half mirror 24 and is reflected by the half mirror 25 and the total reflection mirror 51a, as indicated by the alternate long and two short dashes line in FIG. 3. The reflected light is imaged by the diaphragm 61 and then strikes the light sensor 62.

As the cornea C is gradually deformed, a quantity of light received by the light sensor 62 increases. The light sensor 62 outputs an increase signal relative to the deformation of the cornea C. Based on the increase signal output by the light sensor 62 and the pressure within the cylinder 75 detected by the pressure sensor 78, namely, the pressure of pulsed air, the control circuit 86 measures eye pressure within the eye E under a known process.

After jetting the pulsed air, the piston 76 is slid down and, as a result, the outside air is inhaled into the cylinder 75. Disadvantageously, together with the outside air, tears scattered by the jet of the pulsed air and the like are frequently taken therein. Accordingly, the nozzle 18 and the glass 17 are stained with these impurities whenever the measurement is taken. However, the operator can objectively ascertain an opportunity for washing and cleaning the nozzle 18 and the glass 17 because the monitor M indicates the number set forth by the counter 82. The counter 82 begins to count up simultaneously with the actuation of the driver 81 and counts the number of times which pulsed air has been jetted from the nozzle 18.

Further, it is possible to objectively ascertain the obsolescence of the air injection device 70 from the indication of the number of times the pulsed air has been jetted and, accordingly, make the replacement of the used air injection device 70 opportunely. Instead of the monitor M, an exclusive count displaying means may be used to display the number of times of the jet.

In the above embodiment, the quantity of light emitted by the LED 31 and the detection sensitivity of the corneal deformation detecting optical system 60 are constant regardless of a count obtained by the counter 82. Instead, according to the count, the quantity of light emitted thereby may be increased or the detection sensitivity thereof may be heightened. These improvements make it possible to prevent measurement errors caused by the stained glass 17.

In this case, the control circuit 86 (quantity-of-light regulating means, sensitivity regulating means) serves to increase the quantity of light emitted by the LED 31 in accordance with the count of the counter 86 or heighten the detection sensitivity.

Figure 6:
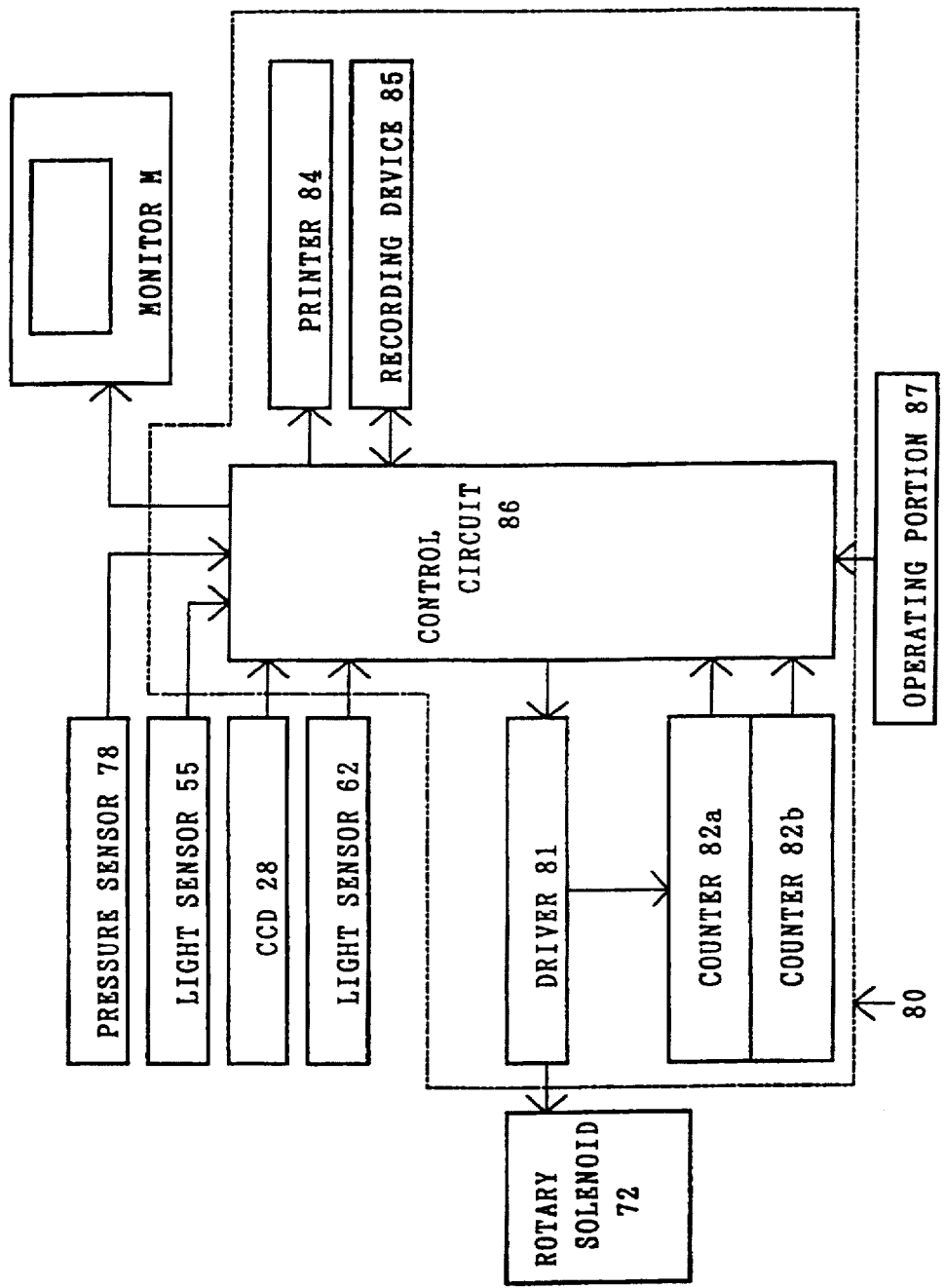
FIG. 6 is a block diagram of a control system of the noncontact tonometer according to a second embodiment of the present invention.

FIG. 6 shows a second embodiment of the present invention. In the second embodiment, the control unit 80 includes two counters 82a, 82b of which respective counts are displayed on the monitor M. The counter 82a is capable of being reset, whereas the counter 82b is incapable of being reset.

The counter 82a is reset to start again from "1" whenever the operator washes and cleans stained optical members in order to indicate an opportunity for washing and cleaning them.

On the other hand, the counter 82b counts up without reset in order to give the operator information different from the washing time, namely, predictive information as to what has caused mechanical troubles or how much the instrument has worn down. In other words, according to a count made by the counter 82b, instructions or warnings can be given in the form of, for example, "Measurement has been already made N times. The expected life of the pressure generating portion has finished. Replace the cartridge soon," or "Measurement has been already made N times. Make periodical inspection."

In the second embodiment, the two counters 82a, 82b are used. Instead, three or more counters may be used in accordance with the number of contents of instructions and be each reset after carrying out the respective instructions.

In the above embodiments, a description was given of the noncontact type of tonometer in which light is projected onto the cornea through the nozzle 18 and the glass 17 and then light reflected by the cornea is received through them. However, the present invention is, of course, applicable to another noncontact type of tonometer in which light is projected onto the cornea not through the nozzle 18 but through a cover glass holding the nozzle 18.

What is claimed is:

1. A noncontact tonometer comprising:

fluid jetting means for jetting a fluid from a nozzle onto a cornea of an eye of a subject;

light projecting means for projecting a beam of light onto the cornea;

deformation detecting means for detecting deformation of the cornea; and counting means for counting the number of times which said fluid jetting means has jetted the fluid so that it can be determined when the nozzle is to be washed.

2. A noncontact tonometer as recited in claim 1, wherein a plurality of counting means are provided.

3. A noncontact tonometer as recited in claim 1, further comprising display means for displaying the number counted by said counting means.

4. A noncontact tonometer as recited in claim 1, further comprising an anterior segment observing optical system having a monitor for observing an anterior segment of the eye and for displaying the number counted by said counting means.

5. A noncontact tonometer comprising:

fluid jetting means for jetting a fluid from a nozzle onto a cornea of an eye of a subject;

light projecting means for projecting a beam of light onto the cornea;

deformation detecting means for detecting deformation of the cornea;

counting means for counting the number of times which said fluid jetting means has jetted the fluid; and quantity-of-light regulating means for regulating a quantity of light projected by said light projecting means so as not to produce a measurement error.

6. A noncontact tonometer comprising:

fluid jetting means for jetting a fluid from a nozzle onto a cornea of an eye of a subject;

light projecting means for projecting a beam of light onto the cornea;

deformation detecting means for detecting deformation of the cornea;

counting means for counting the number of times which said fluid jetting means has jetted the fluid; and sensitivity regulating means for regulating a detection sensitivity of said deformation detecting means so as not to produce a measurement error.

7. A noncontact tonometer as recited in either of claims 5 or 6, further comprising display means for displaying the number counted by said counting means.

8. A noncontact tonometer as recited in either of claims 5 or 6, further comprising an anterior segment observing optical system having a monitor for observing an anterior segment of the eye and for displaying the number counted by said counting means.

* * * * *